(12) United States Patent
Sasaki et al.

(10) Patent No.: US 6,193,933 B1
(45) Date of Patent: Feb. 27, 2001

(54) AUTOMATIC ANALYSIS APPARATUS

(75) Inventors: Yasuhiko Sasaki, Ibaraki-ken; Ryo Miyake, Tsukuba; Akira Koide, Ibaraki-ken; Takao Terayama, Ushiku; Hiroshi Mitsumaki, Mito; Hiroyasu Uchida, Hitachinaka, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/179,090

(22) Filed: Oct. 27, 1998

(30) Foreign Application Priority Data

Oct. 27, 1997 (JP) .................................................. 9-293760
Mar. 10, 1998 (JP) ................................................ 10-057700

(51) Int. Cl.⁷ .......................... G01N 35/00; G01N 35/02
(52) U.S. Cl. ............................ 422/64; 422/63; 422/100; 422/102; 422/104; 436/43; 436/45; 436/47; 436/49; 436/54; 436/180
(58) Field of Search .................... 422/63, 64, 100, 422/102, 104; 436/43, 45, 47, 49, 54, 180; 417/413.1, 413.2

(56) References Cited

U.S. PATENT DOCUMENTS

| | | | | |
|---|---|---|---|---|
| 4,738,826 | * | 4/1988 | Harris | 422/100 |
| 4,764,342 | * | 8/1988 | Kelln et al. | 422/72 |
| 4,844,868 | * | 7/1989 | Rokugawa | 422/64 |
| 5,173,741 | * | 12/1992 | Wakatake | 356/246 |
| 5,232,664 | * | 8/1993 | Krawzak et al. | 422/64 |
| 5,262,049 | * | 11/1993 | Ferkany | 210/258 |
| 5,413,246 | * | 5/1995 | Godolphin et al. | 222/1 |
| 5,424,036 | * | 6/1995 | Ushikubo | 422/64 |
| 5,434,083 | * | 7/1995 | Mitsumaki et al. | 436/48 |
| 5,439,646 | * | 8/1995 | Tanimizu et al. | 422/64 |

FOREIGN PATENT DOCUMENTS

WO 83/00932 * 3/1983 (WO) ............................ G01N/37/00

* cited by examiner

Primary Examiner—Jill Warden
Assistant Examiner—Kath Bex
(74) Attorney, Agent, or Firm—Antonelli, Terry, Stout & Kraus, LLP

(57) ABSTRACT

Heretofore, there has been demanded an automatic analysis apparatus which can prevent cross-contamination between reagents, which can prevent dust and gas from entering a reagent supply device, which can always know a remaining quantity of the reagent while can reduce the quantity of waste. According to the present invention, there is provided an automatic analysis apparatus in which a reagent supply device for supplying a reagent from a reagent container into a reaction container is removably attached to the reagent container, a protective door is provided in the reagent supply port in order to aim at preventing dust from entering the reagent supply device, and further the reagent container and the reagent supply device are provided with recording mediums for recording therein conditions thereof, a time of replacement thereof or the like, and which can inform whether the setting is proper or not.

13 Claims, 16 Drawing Sheets a: SEPARATING STEP b: DISCHARGING STEP c: MOUNTING STEP a: SEPARATING STEP b: WASHING STEP c: SEALING STEP d: FILLING STEP e: MOUNTING STEP

CONNECTABLE

UNCONNECTABLE

AUTOMATIC ANALYSIS APPARATUS

BACKGROUND OF THE INVENTION

The present invention relates to an automatic analysis apparatus for quantifying a density of a substance dissolved in liquid, and in particular, to an automatic analysis apparatus for analyzing components of biological fluid, water or the like.

A conventional automatic analysis apparatus is disclosed in Japanese Laid-Open Patent No. S63-131066. A reagent container used in this apparatus, is composed of a chamber part in which a reagent is held, a pump part integrally incorporated with the chamber part, for sucking and pipetting the reagent from the chamber part by a predetermined quantity, and a pipette removably attached to a reagent discharge outlet port of the pump part. Further, a liquid filling port is formed in the upper part of the chamber part, and is removably fitted thereto with a cap formed therein with a vent hole for holding the inside of the chamber part at the ambient atmospheric pressure. Since the reagent container is integrally incorporated with the pump part, a system which can prevent carry-over of a reagent and cross-contamination is used.

The above-mentioned prior art fails to disclose any of countermeasures against the following problems:

First, the reagent container has a complicated structure so as to be expensive since it is integrally incorporated with the pump part as a reagent discharging means. Further, the volume of waste materials is increased, resulting in waste of resources since the reagent container is thrown away together with the pump part.

Second, since no data recording medium is provided to either the reagent container or the pump part, it is difficult to obtain data relating to a kind of a reagent, a used quantity, a remaining quantity, a quality, a condition of the pump part or the like.

Third, sticking of dust or contamination to the reagent supply port of the container, and deposition of solid components in the reagent due to drying of the reagent are caused, resulting in risks of clogging of the reagent supply port, and entry of foreign matter during discharge of the reagent, since the pipetter as a reagent discharge outlet is exposed.

Fourth, since the reagent container has such a structure that gas within the container flows into a passage, the degree of accuracy in a supply quantity of a reagent upon pipetting becomes uneven.

OBJECT AND SUMMERY OF THE INVENTION

An objet of the present invention is to provide an automatic analysis apparatus which can solve the above-mentioned problems, which is small-sized and which can simply carry out analysis with a high degree of accuracy.

According to the present invention, there is provided an automatic analysis apparatus in which a reagent container is removably attached to a reagent supply device, that is, the reagent supply device is attached to the reagent container which is then installed in the automatic analysis apparatus.

The reagent container or the reagent supply device is incorporated therein with data recording medium which can be accessed by a data recording and reproducing device incorporated in the automatic analysis apparatus in order to read and write data from and to the data recording medium.

Further, an openable and closable door is provided in the reagent supply port of the reagent supply device, which covers the reagent supply port when no reagent is discharge, but which is operated so as to open the reagent supply port when the reagent is to be discharged.

Further, a reagent bag in which a reagent is charge fully, is provided in the reagent container.

BRIEF DESCRIPTION OF THE DRAWINGS

FIG. 1b is a front view illustrating the automatic analysis apparatus shown in FIG. 1a;

FIG. 2a is a perspective view illustrating a reagent container shown in FIG. 1a;

FIG. 2b is a perspective view illustrating a pump unit shown in FIG. 1a;

DESCRIPTION OF THE PREFERRED EMBODIMENTS OF THE INVENTION
DESCRIPTION OF THE EMBODIMENTS

Figure 1A:
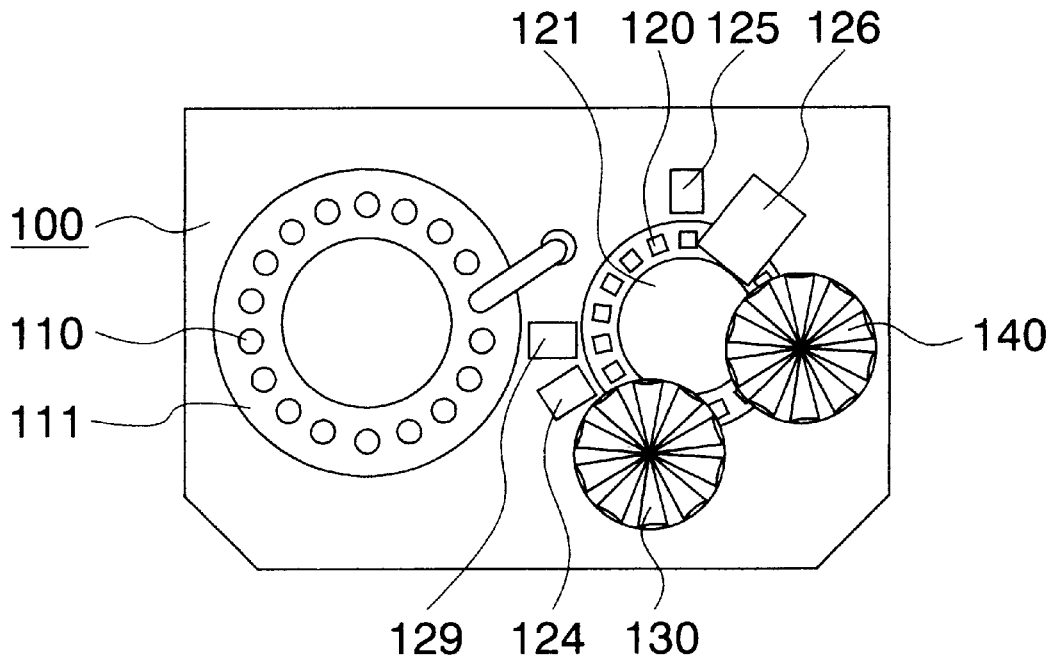
FIG. 1a is a top view illustrating an automatic analysis apparatus in an embodiment of the present invention.
Figure 1B:
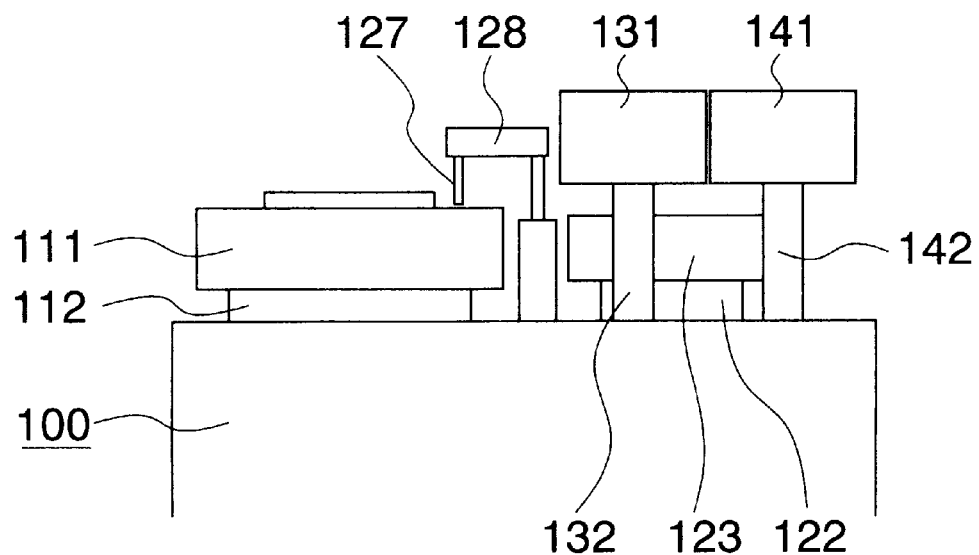

FIGS. 1a to 1b are a top plan view and a front view which show an automatic analysis apparatus in its entirety.

The automatic analysis apparatus in this embodiment is composed of a sample holder 111 in which at least one of sample containers 110 containing a sample to be measured, can be accommodated; and a sample container holder rotating drive mechanism 112 for conveying the sample container 110 accommodated in the sample container holder 111 to a sample sucking position.

Further, the automatic analysis apparatus comprises a reaction container holder 121 for accommodating at least one of reaction containers 120 in which at least one kind of reagent is added to the sample for reaction between the reagent and the sample, and a reaction container holder rotating drive mechanism 122 for conveying the reaction container 120 accommodated in the sample container holder 121 to a sample discharge position, a first reagent discharge position and a second reagent discharge position, successively.

Further, it comprises a sample pipetter 128 for inserting a nozzle 127 into a sample container 120 which has been conveyed to the sample sucking position, so as to suck the sample from the sample container 120 in order to pipette the sample by a predetermined quantity into a reaction container 120 which has be conveyed to the sample discharge position, and a sample pipetter washing mechanism 129 for washing the sample pipetter. It is noted here that the reaction container holder is in the form of a thermostat oven 123 for maintaining the reagent and the sample in the reaction container 120 at a predetermined temperature.

Further, there are provided first reagent containers 130 in which a first reagent is held, corresponding to an measuring item, a first reagent container holder 131 for accommodating at least one of the first reagent containers 130, and a first reagent container holder rotating drive mechanism 132 for conveying a first reagent container 130 accommodated in the first reagent container holder 131, to the first reagent discharge position.

Further, there is provided a first reagent pump unit (denoted by reference numeral 160 in FIG. 2) serving as a reagent supply device for pipetting the first reagent by a predetermined quantity from a first reagent container which has been conveyed to the first reagent discharge position into a reaction container 120 containing therein a sample, at the first reagent discharge position.

Further, there are provided a second reagent container holder 141 for accommodating at least one of second reagent containers 140 in which a second reagent corresponding to a measuring item is held, a second reagent container holder rotating drive mechanism 142 for conveying the second reagent container 140 accommodated in the second reagent container holder 141 to the second reagent discharge position, and a second reagent pump unit (having the same structure as that of the first reagent pump unit) for pipetting a predetermined quantity of the second reagent from a second reagent container having been conveyed to the second reagent discharge position into the reaction container 120 which is located at the second reagent discharge position and in which the sample and the first reagent are contained.

Further, there are provided an agitating mechanism 124 for mixing the sample with at least one kind of reagent which are contained in the reaction container 120, a spectrometric measuring part 125 for measuring a variation in absorbency of the sample contained in the reagent container, caused by reaction with at least one kind of reagent, and a reaction container washing mechanism 126 for washing the reaction container 120 after the spectrometric measurement is completed.

Explanation will be made of the reagent container and the pump unit in detail.

Figure 2A:
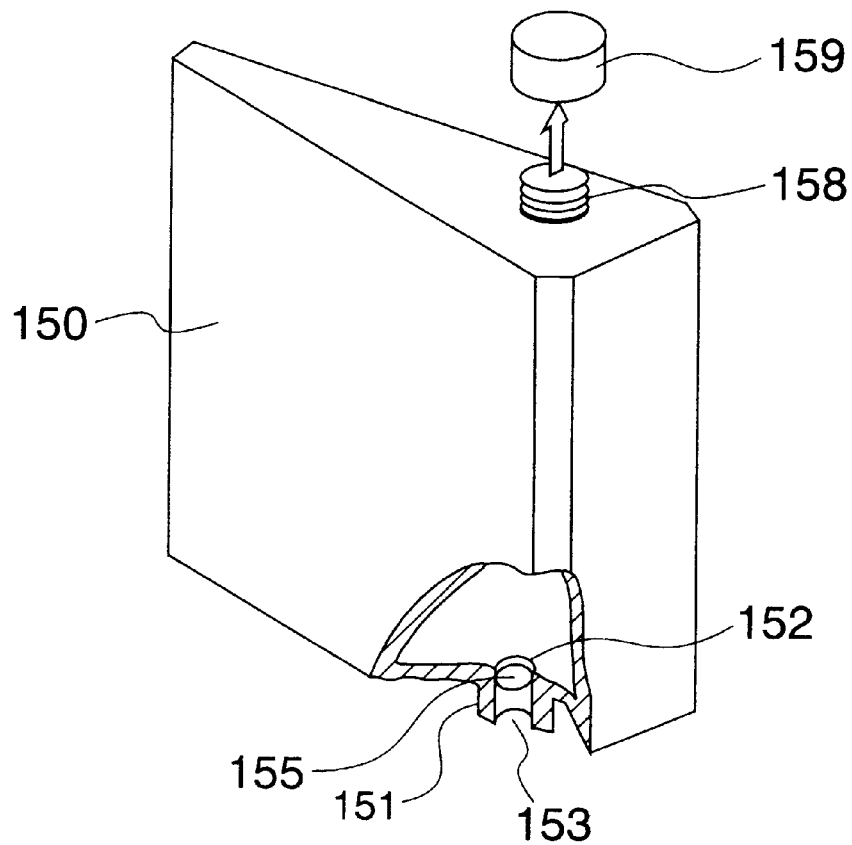
Figure 2B:
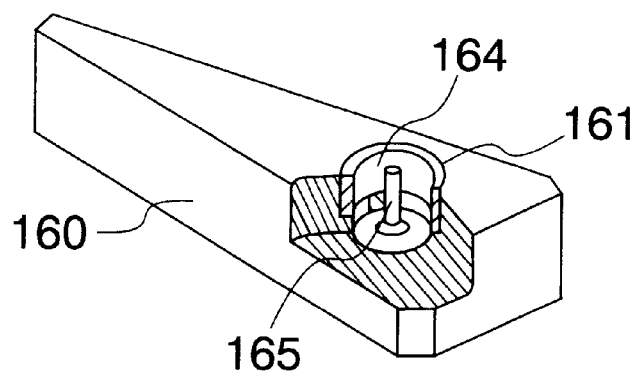

Referring to FIG. 2, a reagent container 150 corresponding to the reagent containers 130, 140 in which the first and second reagents are held, and a pump unit 160 as a reagent supply device will be explained.

The reagent container 150 is provided with a suction port 158 and a reagent side connection part 151. The suction port 158 is attached thereto with a removable cap 159. When the removable cap 159 is removed, the pressure in the reagent container 150 can be held at a pressure substantially equal to the ambient atmospheric pressure.

The reagent container side connection part 151 has a pipe-like shape, having one of openings, serving as a reagent inlet port 152 and positioned inside of the reagent container 150, and the other one of openings, serving as a reagent container reagent outlet port 153 and positioned outside of the reagent container 150.

It is noted that when the reagent container 150 is accommodated in the reagent container holder 111, the posture of the reagent container 150 is preferably such that the reagent container side reagent inlet port 152 is located on the bottom surface side of the reagent container 150.

At least one of seals 155 is attached between the reagent container side reagent inlet port 152 and the reagent container reagent outlet port 153 of the reagent container side connection part 151, and accordingly, the reagent cannot come out from the reagent container 150 through the reagent container reagent inlet port 153 when the reagent is not used.

The pump unit 160 is provided with a pump unit side connection part 161 in the form of a hole, and the pump unit side connection part 161 is provided therein with a seal member 164 for preventing the reagent from leaking, which is packed in a gap between the reagent container side connection part 151 and the pump side connection part 161 on the inside of the pump unit side connection part 161 when the reagent container 150 is mounted on the pump unit 160.

Further, the pump unit connection part 161 is provided with a protrusion 165 for opening the seal 155 when the pump unit 160 is mounted to the reagent container 150.

Figure 3:
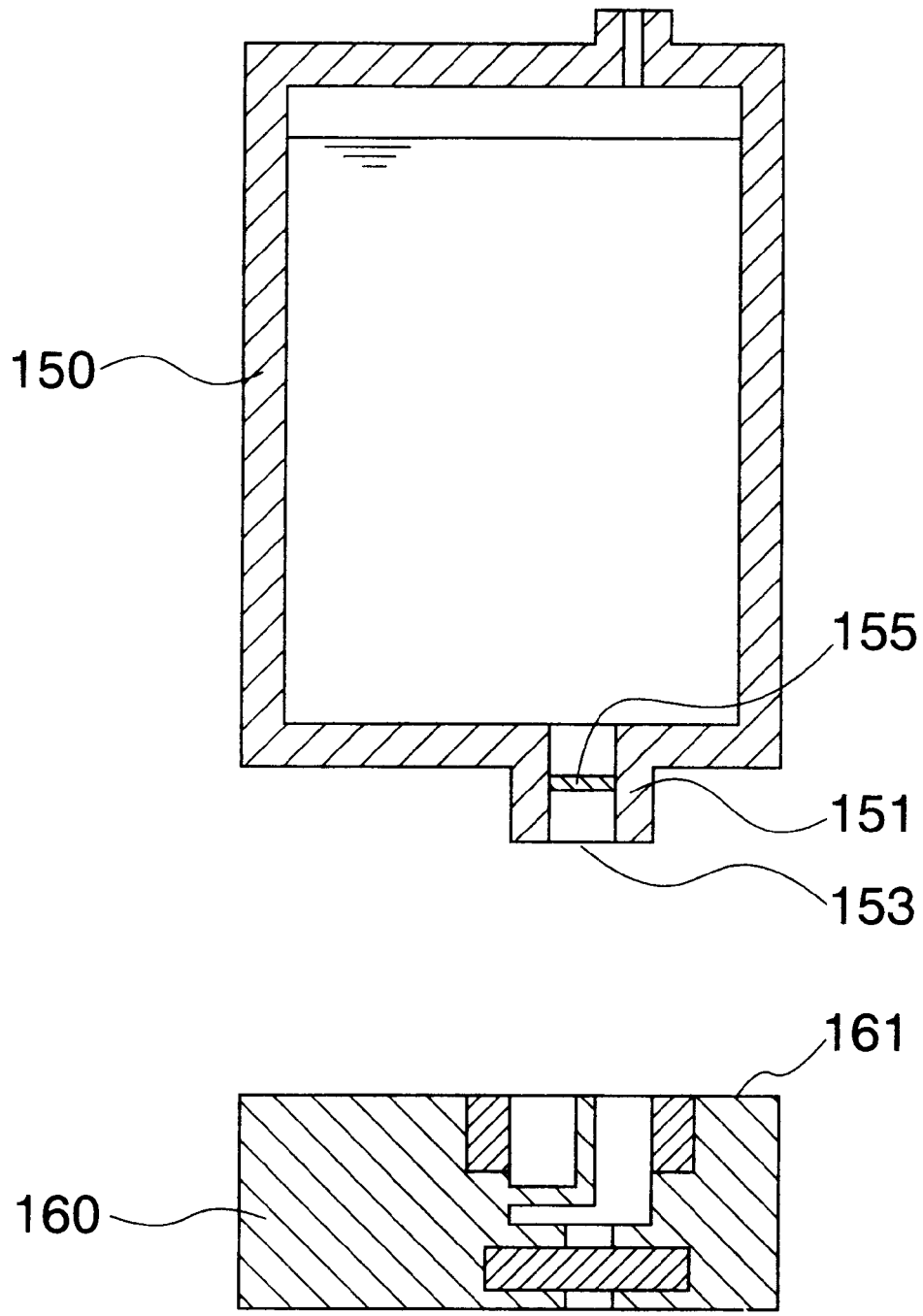
FIG. 3 is a sectional view for explaining details of the reagent container and the pump unit shown in FIGS. 2a and 2b.
Figure 4A:
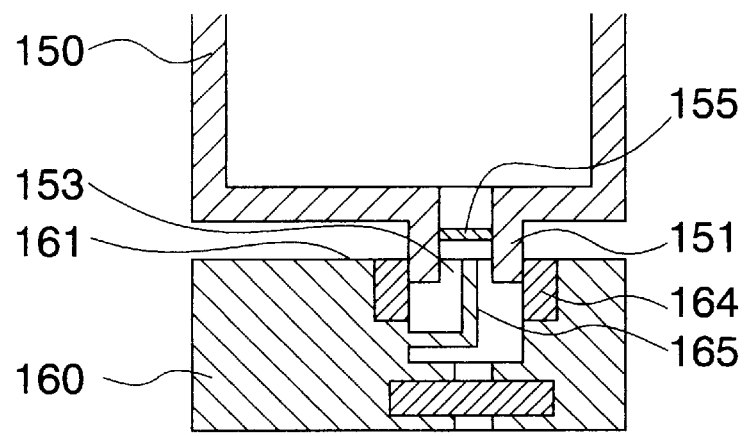
FIG. 4a is a sectional view for explaining a condition in which the reagent container and the pump unit are on the way of installation.
Figure 4B:
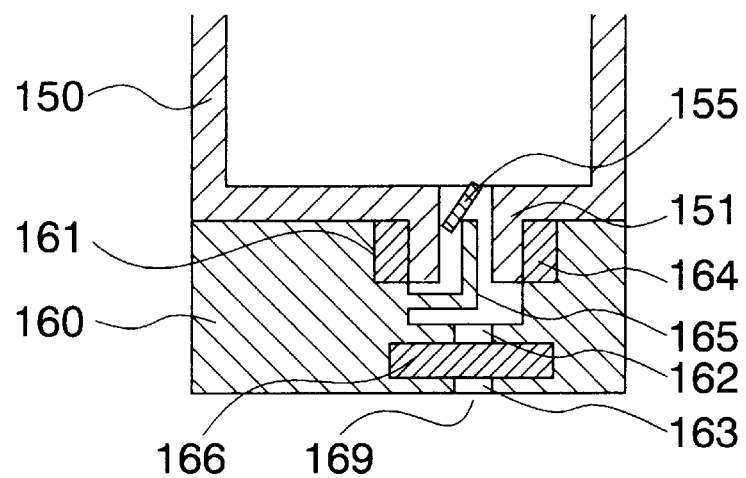
FIG. 4b is a sectional view for explaining a condition in which the reagent container and the pump part have been installed.
Figure 4B:
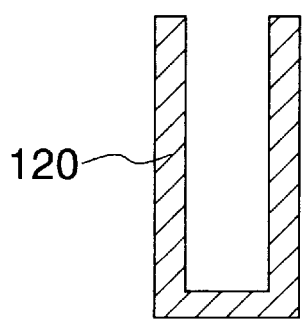

Referring to FIGS. 3 and 4, explanation will be made of the steps of attaching the pump unit 160 to the reagent container 150.

Referring to FIG. 3, the reagent container 150 and the pump unit 160 are not yet made into contact with each other. At this time, the seal 155 blocks the reagent container reagent outlet port 153, and accordingly, the reagent cannot come out from the reagent container 150. Further, the reagent container side connection part 151 and the pump unit side connection part 161 are not yet connected with each other.

Referring to FIG. 4a which shows such a condition that the reagent container side connection part 151 of the reagent container 150 is made into contact with the seal member 164 in the pump unit side connection part 161 of the pump unit 164, but the seal 155 is not made into contact with the protrusion 164, the seal member 165 fills in the gap between the reagent container side connection part 151 and the pump unit side connection part 161 so as to seal the gap. Further, a seal 155 blocks the reagent container side reagent outlet port 153, and accordingly, the reagent does not come out from the reagent container 150, and then flows into the pump unit 160.

Referring to FIG. 4b which shows such a condition that the reagent container side connection part 151 of the reagent container 150 is made into contact with the seal member 164 in the pump unit side connection part 151 of the pump unit 150, and the seal 155 is broken after being made into contact with the protrusion 165. Thus, the reagent can flow into the pump unit 1 from the reagent container 150.

Referring to FIG. 4b, the steps of discharging the reagent from the reagent container 150 into the reaction container 120.

When the pump part 166 in the pump unit 160 sucks the reagent, the reagent flows through the reagent container side connection part 151 formed in the reagent container 150, and then through the pump side connection part 161 and the passage 162 formed in the pump unit 160, and then flows into the pump unit 160. The pump unit 160 then discharge the reagent through the passage 163 and the discharge outlet port 169 and into the reaction container 120, by a predetermined quantity. It is noted that the lengths of the flow passage 162 and the flow passage 163 are preferably set to be short as possible as it can.

Figure 5:
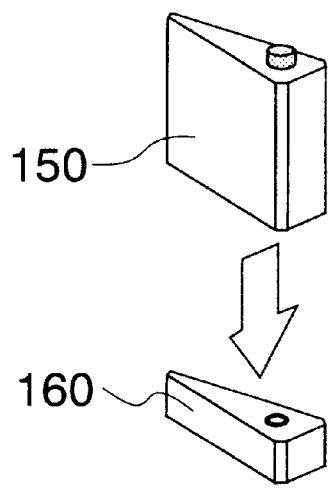
FIG. 5 is a perspective view for explaining the steps of discarding a reagent container.
Figure 5:
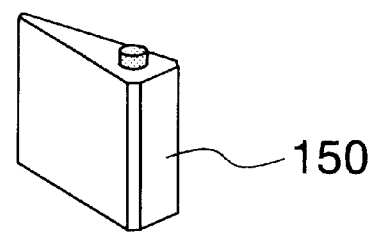
Figure 5:
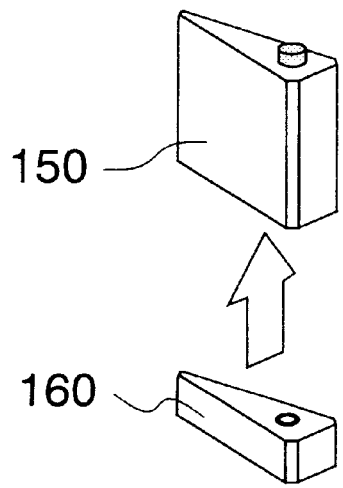

Referring to FIG. 5, explanation will be made of steps of discarding the reagent container 150 and the steps of reusing the pump unit 160 after the reagent is exhausted from the reagent container 150.

When the reagent container 150 is discarded after the reagent is exhausted therefrom, the pump unit 160 is separated from the reagent container 150 at a separating step a, and then, only the reagent container 150 is discarded at a discarding step b. Meanwhile, the pump unit 160 is mounted to another reagent container 150 in which the same kind of reagent as that held in the former reagent container 150 is contained, at a mounting step c, and is therefore used again in the automatic analysis apparatus.

Figure 6:
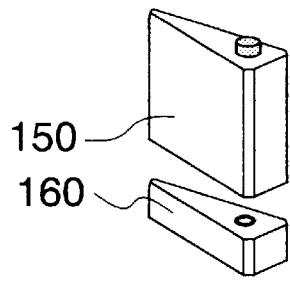
FIG. 6 is a perspective view for explaining reuse of the reagent container and the pump part shown in FIGS. 2a, and 2b.
Figure 6:
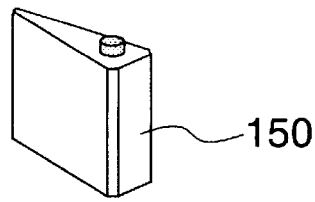
Figure 6:
Figure 6:
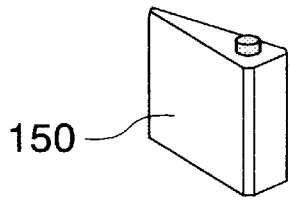
Figure 6:
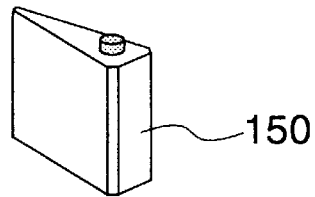
Figure 6:
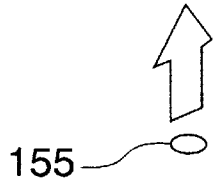
Figure 6:
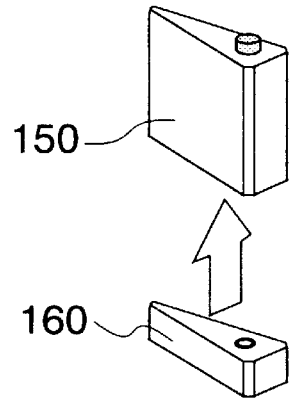

Since the pump unit which is relatively expensive can be reused, the higher the degree of use frequency, the lower the cost. Further, the steps of reusing the pump unit and also the reagent container will be explained with reference to FIG. 6.

In the case of reusing the reagent container from which a reagent is exhausted, at first, the pump unit 160 is separated from the reagent container 150 at a separating step a. Then, the reagent container 150 is washed with washing liquid and detergent. Next, the reagent container side connection part 151 is blocked by the seal 155 at a blocking step c. Further, the same reagent as that having been held previously in the reagent container 150 is filled in the same reagent container 150 at a filling step. Then, the pump unit 160 is mounted to the reagent container 150 in which the reagent has been filled, at a mounting step e, and is then used again in the automatic analysis apparatus.

As mentioned above, since the reagent container 150 and the pump unit 160 are separatable from each other, it is possible to prevent occurrence of cross-contamination between different kinds of reagents. Further, since only the reagent container 150 is discarded while the pump unit 160 is reused in the case of discard after use, the cost of the reagent container 150 can be lowered, and the quantity of waste can be decreased. In the case of reusing the reagent container and the pump unit, since only the reagent container is washed after use, the degrees of consumption of the washing liquid and the detergent can be lowered, and further, the time of the washing can be shortened.

It is noted that in addition to this embodiment, even though the reagent container side connection part 151 of the reagent container 150 is in the form of a hole while the pump unit side connection part 161 of the pump unit 160 is in the form of a pipe, effects similar to those mentioned above can be obtained.

Explanation will be made of a second embodiment of the present invention with reference to the drawings.

Figure 7A:
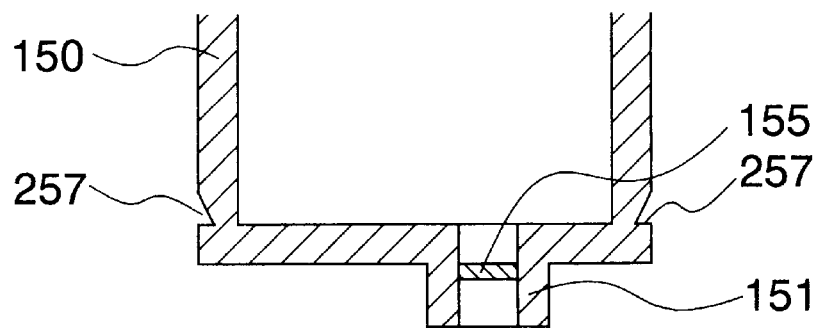
FIG. 7a is a sectional view illustrating a reagent container and a pump unit in a second embodiment of the present invention.
Figure 7A:
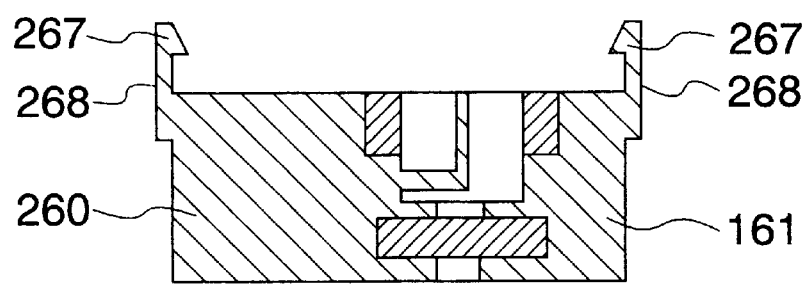
Figure 7B:
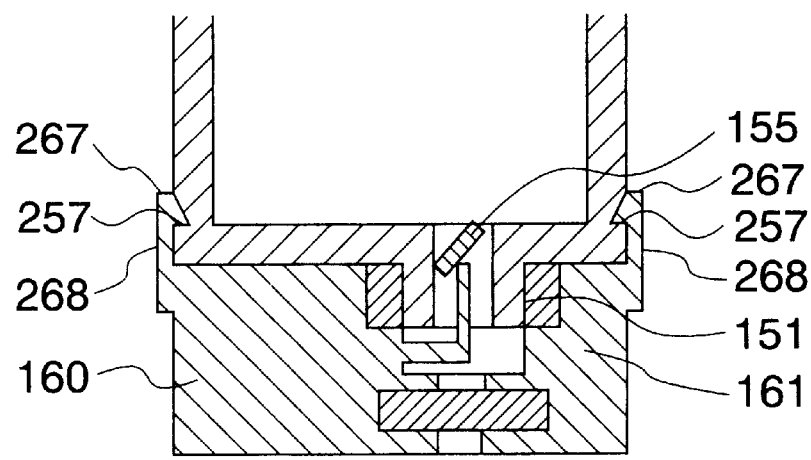
FIG. 7b is a sectional view for explaining a condition in which the reagent container and the pump unit shown in FIG. 7a are installed.

Referring to FIGS. 7a and 7b which show such an arrangement that the reagent container and the pump unit are surely fixed, and in which like reference numerals are used to denote like components to those explained in the first embodiment, the arrangement of the second embodiment is substantially the same as that of the first embodiment, except that fixing parts are provided in order to fix the reagent container 150 and the pump unit 160.

Namely, in addition to the structure explained in the first embodiment, the reagent container 150 is formed therein with a fixing recess 257 while the pump unit 160 is provided with a fixing panel 268 formed thereon with a fixing protrusion 267.

As shown in FIG. 7b, when the reagent container 150 is mounted on the pump unit 160, the fixing protrusion 267 formed on the fixing panel 268 of the pump unit 160 is fitted in the fixing recess 257 of the reagent container 150.

Thus, with the provision of the fixing panel 268 in the pump unit 160 as mentioned above, the reagent container 150 and the pump unit 160 which have been fixed together, can be prevented from positionally deviating in a rotating direction around an axis in the direction of insertion thereof.

Further, with the provision of the fixing recess 257 in the reagent container and the fixing protrusion 267 in the pump unit 160, the reagent container 150 and the pump unit 160 which have been fixed together, can be prevented from positionally deviating in the direction of insertion thereof.

Effects similar to the above-mentioned embodiment can be obtained, even if the reagent container 150 is provided with a fixing panel formed thereon with a fixing protrusion while the pump unit 160 is formed therein with a fixing recess, or the fixing panel is formed therein with a fixing recess while the other one is formed therein with a fixing protrusion.

Explanation will be made of a third embodiment of the present invention with reference to FIGS. 8a to 8b.

The arrangement of the third embodiment is substantially the same as that of the first embodiment, except that the reagent container side connection part 151 of the reagent container 150 is formed with a male thread part while the pump unit side connection part 161 of the pump unit 160 is formed therein with a female thread part. Further, the reagent container 150 is provided with a fixing recess 357 while the pump unit 160 is formed thereon with a fixing protrusion 367.

Next, the steps of mounting the pump unit 160 to the reagent container 150 will be explained.

Figure 8:
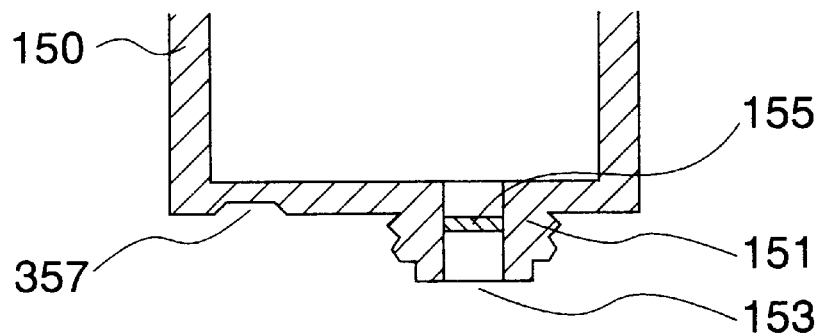
FIG. 8a is a sectional view illustrating a reagent container and a pump unit in a third embodiment of the present invention.
FIG. 8b is a sectional view for explaining a condition in which the reagent container and the pump unit shown in FIG. 8a are installed.
Figure 8:
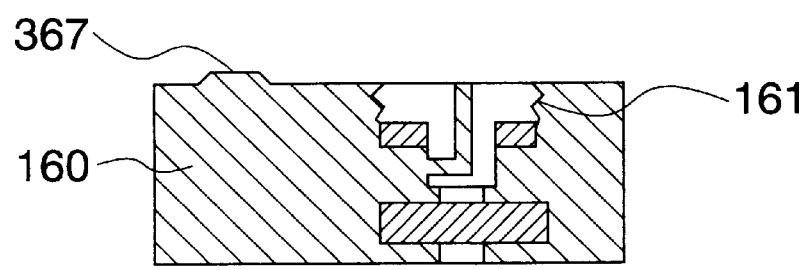
Figure 8:
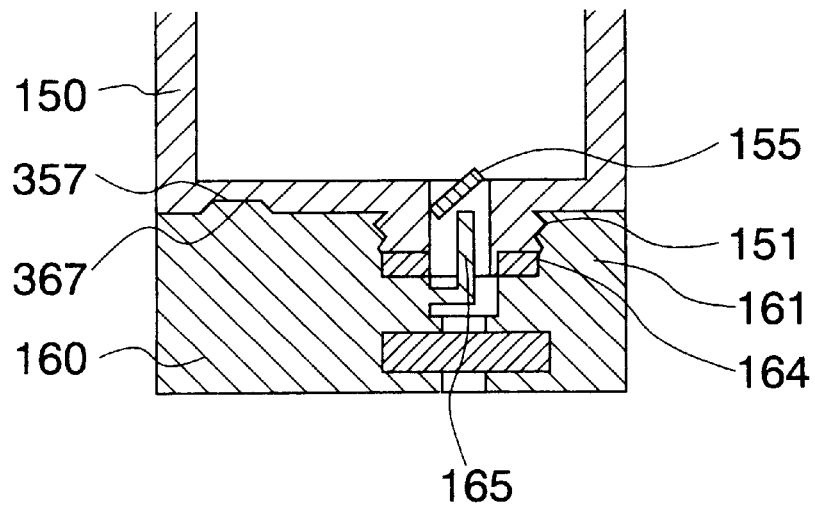

Reference to FIG. 8a which shows such a condition that the reagent container 150 and the pump unit 160 are not made into contact with each other, the reagent container side connection part 151 is blocked by the seal 155, and accordingly, the reagent does not come out from the reagent container 150. Further, no sealing is made between the reagent container side connection part 151 and the pump unit side connection part 161.

Next, when the connection is started, the reagent container side connection part 151 of the reagent container 150 is made into contact with the seal member 164 in the pump unit side connection part 161 of the pump unit 160, but the seal 155 is not yet made into contact with the protrusion 165. At this time, the seal member 164 fills in the gap between the reagent container side connection part 151 and the pump unit side connection part 161 so as to seal the gap. Further, the seal 155 blocks the reagent container side connection part 151, and accordingly, the reagent does not comes out from the reagent container 150.

Further, as the connection is progressed, as shown in FIG. 8b, the reagent container side connection part 151 of the reagent container 150 is made into contact with the seal member 164 in the pump side connection part 160, and the seal 155 is broken since it is made into contact with the protrusion 165. At this time, the seal member 164 fills the gap between the reagent container side connection part 151 of the reagent container 150 and the pump side connection part 161 of the pump unit 160 for sealing the gap. Further since the seal 166 in the reagent container side connection part 151 is broken, the reagent comes out from the reagent container 150, and then flows into the pump unit 160.

In this condition, the fixing protrusion 367 of the pump unit 160 is inserted into the fixing recess 357 of the reagent container 150, and further, by fastening the threaded parts, any positional deviation in the rotating direction can be prevented after the mounting.

As mentioned above, since the threads are formed in the reagent container side connection part 151 of the reagent container and the pump unit side connection part 161 of the pump unit 160, and since the fixing recess 357 and the fixing protrusion 367 are formed in the reagent container 150 and the pump unit 160, respectively, it is possible to prevent occurrence of positional deviation.

Explanation will be hereinbelow made of a fourth embodiment of the present invention with reference to FIGS. 9 and 10 which show another structure for mounting the pump unit to the reagent container.

Figure 9:
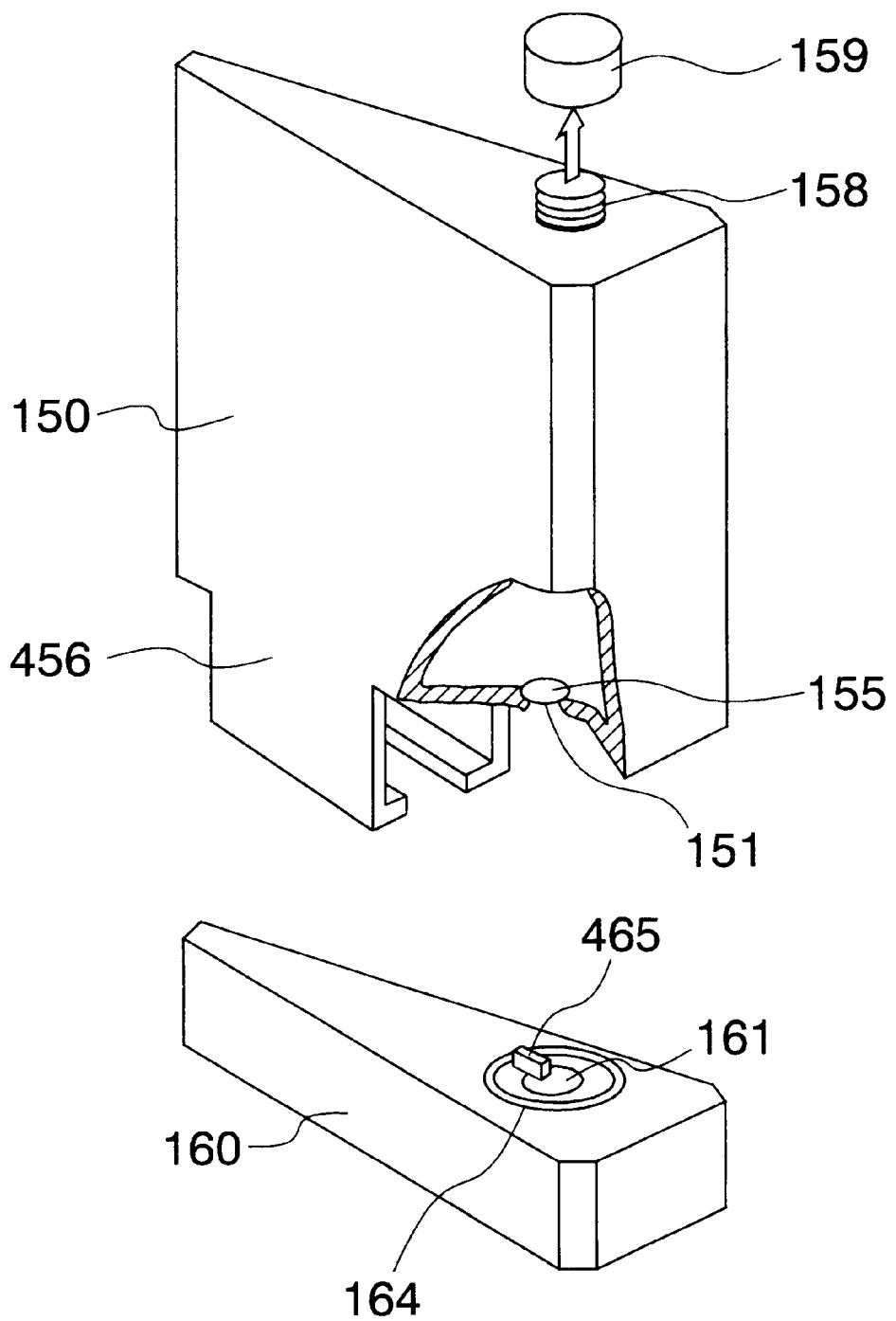
FIG. 9 is a perspective illustrating a reagent container and a pump unit in a fourth embodiment of the present invention.
Figure 10:
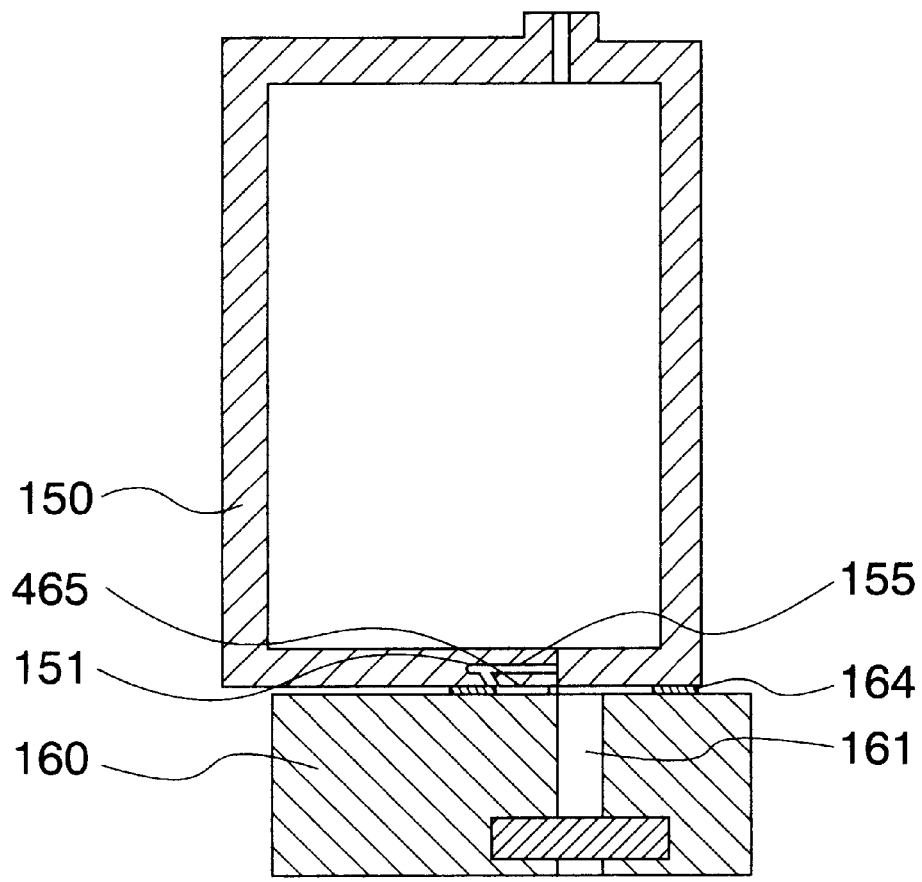
FIG. 10a is a sectional view illustrating the reagent container and the pump unit shown in FIG. 9 on the way of the installation thereof.
FIG. 10b is a sectional view illustrating the reagent container and the pump unit shown in FIG. 9.
Figure 10:
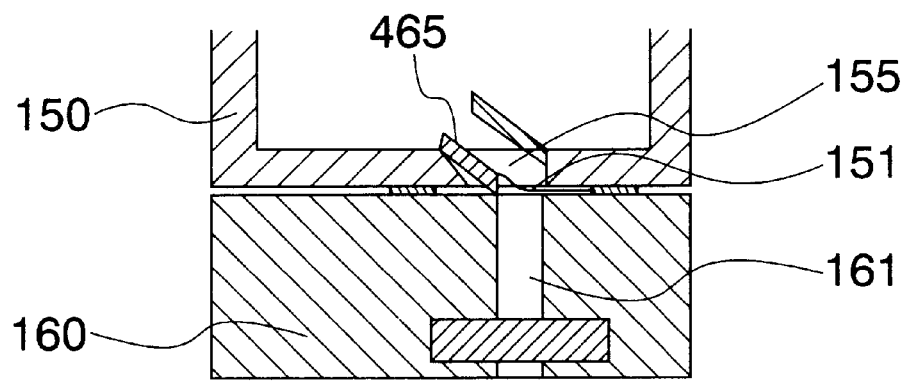

The arrangement of the fourth embodiment is the same as that of the first embodiment, except that the reagent container 150 is formed in its lower part with a connection guide 456 as shown in FIG. 9, and that the seal 155 in the reagent container 150 is openable while the reagent side connection part 151 has such a shape that one side part thereof, as viewed widthwise of the reagent container, diverges inward of the reagent container (as a hole formed therein a slope on one side thereof). Further, the protrusion 465 of the pump unit 160 is guided along a slope of the reagent container side connection part 151 of the reagent container 150, and further, can be deformed. In addition, the seal member 164 is provided being projected from the outer surface of the pump unit 160.

The connection guide 456 serves as a guide for mounting the pump unit 160 to the reagent container 150.

The pump unit side connection part 161 of the pump unit 160 is hole-like, and the seal member 164 provided outside of the pump unit side connection part 161 can prevent leakage through the gap between the reagent container side connection part 151 and the pump unit side connection part 161 after the pump unit 161 is mounted to the reagent container 150.

The protrusion 465 provided around the pump unit side connection part 161 is adapted to open the seal 155 when the pump unit 160 is mounted to the pump unit 150.

The steps of mounting the pump unit 160 to the reagent container 150 will be explained with reference to FIGS. 10 and 10b.

Referring to FIG. 10a which shows such a condition that a surface formed therein with the reagent container side connection part 151 of the reagent container 150 is mated with a surface formed therein with the pump side connection part 161 of the pump unit 160, the protrusion 465 has not yet make contact with the seal 155 which therefore blocks the reagent side connection part 151 so that the reagent does not comes out from the reagent container 150. Further, the seal member 164 seals between the reagent container side connection part 151 and the outer periphery of the pump unit side connection part 160.

FIG. 10b shows such a condition that the pump unit 160 has been slid from the position shown in FIG. 10a so as to be coupled with the reagent container 150.

At this time, the protrusion 465 is deformed along the slope of the reagent container side connection part 151, and finally pushes up the seal 155. Since the seal member 164 seals the reagent container side connection part 151 and the outer periphery of the pump side connection part 161 therearound, no leak occurs, and further, the reagent comes out from the reagent container 150 and then, flows into the pump unit 160.

As mentioned above, since the reagent container 150 is provided with the side connection part 151 which is hole-like, the connection guide 456 and the seal 155, and sine the pump unit 160 is provided with the pump unit side connection part which is hole-like, the seal member 164 and the protrusion 465, the structure of the connection can be simplified, and further, positional deviation after the mounting can be prevented.

Explanation will be made of a fifth embodiment of the present invention with reference to FIGS. 11a and 11b.

Figure 11A:
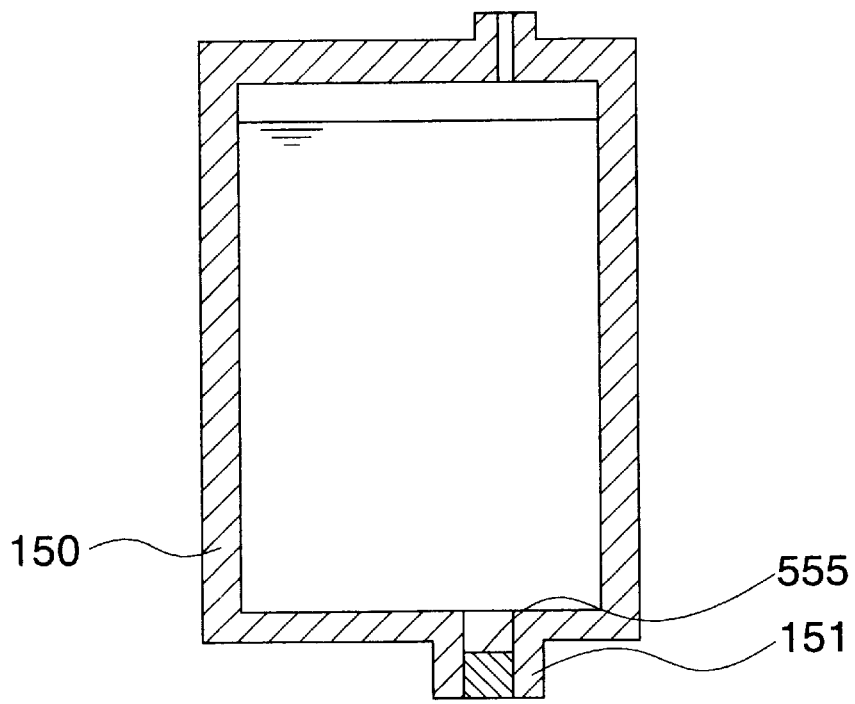
FIG. 11a is a sectional view illustrating a reagent container and a pump unit which are separated from each other.
Figure 11A:
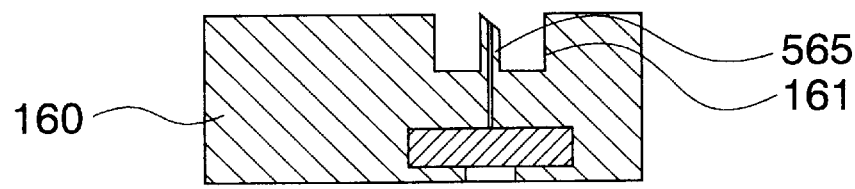
Figure 11B:
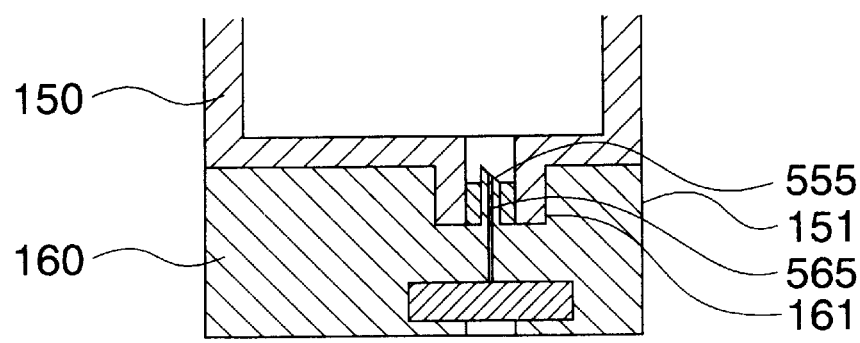
FIG. 11b is a sectional view for illustrating the reagent container and the pump unit which are shown in FIG. 11a and which are separated from each other.

The arrangement of the fifth embodiment shown in FIGS. 11a and 11b is the same as that of the first embodiment, except that the reagent outlet port side of the reagent container side connection part 151 of the reagent container 150 is plugged by a seal member 555, and a hollow needle-like protrusion 565 is provided on the pump unit 1.

The steps of mounting the pump unit 160 to the reagent container 160 will be hereinbelow explained. It is noted that like reference numerals are used to denote like components explained in the first embodiment.

Referring to FIG. 11a which shows a condition that the reagent container 150 is separated from the pump unit 160, and FIG. 11b which shows such a condition that both are coupled together, and accordingly, the hollow needle-like protrusion 565 in the pump unit side connection part 161 of the pump unit 160 pierces through the seal member 555 in the reagent container side connection part 151 of the reagent container 150. At this time, the seal member 555 is elastically deformed so as to seal between itself and the hollow needle-like protrusion 565. However, since the hollow needle-like protrusion 565 pierces through the seal member 555, the reagent comes out from the reagent container 150, and then flows into the pump unit 160.

Next, explanation will be hereinbelow made of the steps of reusing the reagent container 150 and the pump unit after the reagent is exhausted from the reagent container 150. The steps are similar to those shown in FIG. 6.

After exhaustion of the reagent, if the reagent container 150 and the pump unit 160 are reused, at first, the reagent container 150 is separated from the pump unit 160. Then, the reagent container 150 is washed with the use of washing liquid and detergent. Further, the same kind of reagent as that has been contained in the reagent container 150 is charged in the reagent container 150. Thus, the reagent container 150 filled with the reagent is then mounted thereto with the pump unit 260, and is then used in the automatic analysis apparatus.

As mentioned above, since the seal member 555 is provided in the reagent container side connection part 151 of the reagent container 150, and since the hollow needle-like protrusion 565 is provided on the pump unit side connection part 161 of the pump unit 160, the necessity of a step of sealing the reagent container side connection part 151 of the reagent container 150 can be eliminated, thereby it is possible to reduce the cost of reuse.

It is noted that the seal member and the hollow needle-like protrusion may be simply used in not only this embodiment but any of the other embodiment so as to obtain the same effects as stated in this embodiment.

Explanation will be made of a sixth embodiment of the present invention with reference to FIG. 12.

Figure 12:
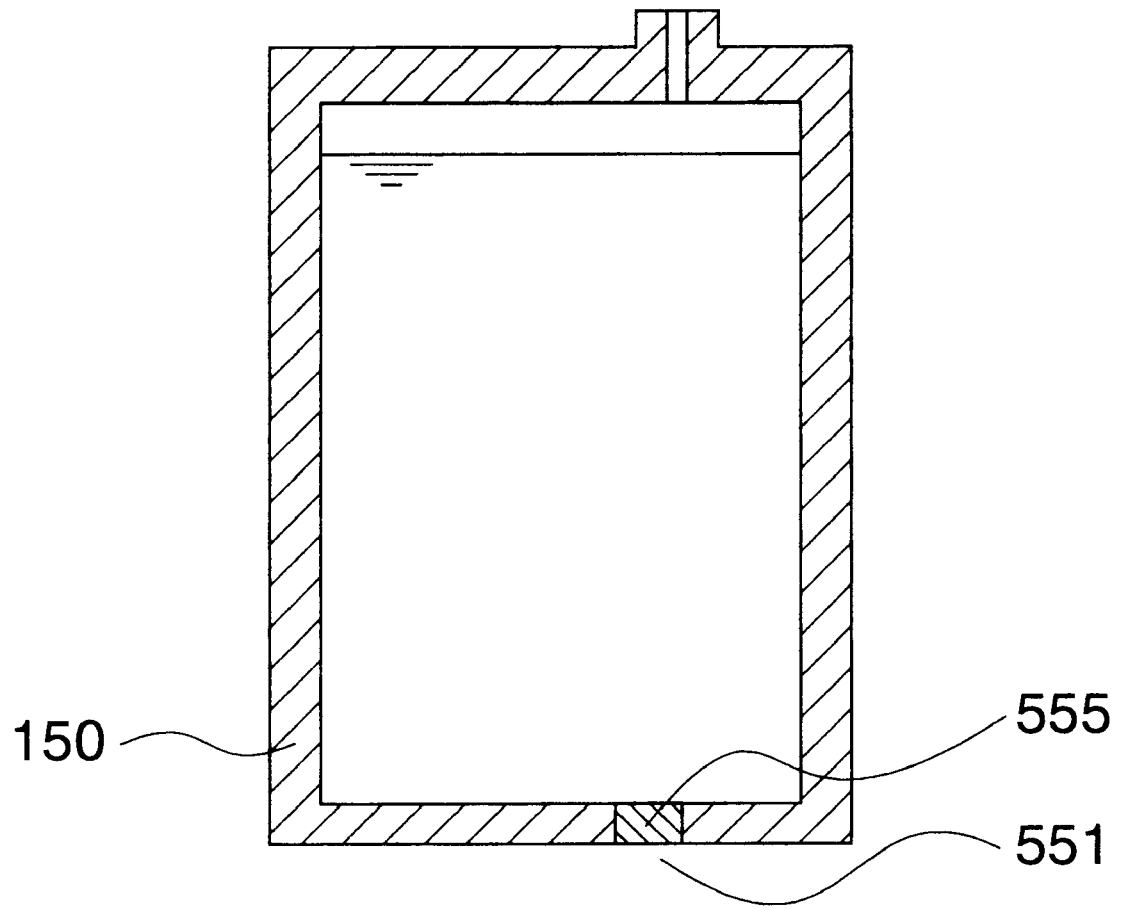
FIG. 12 is a sectional view illustrating a reagent container and a pump unit in a sixth embodiment of the present invention, which are separated from each other.
Figure 12:
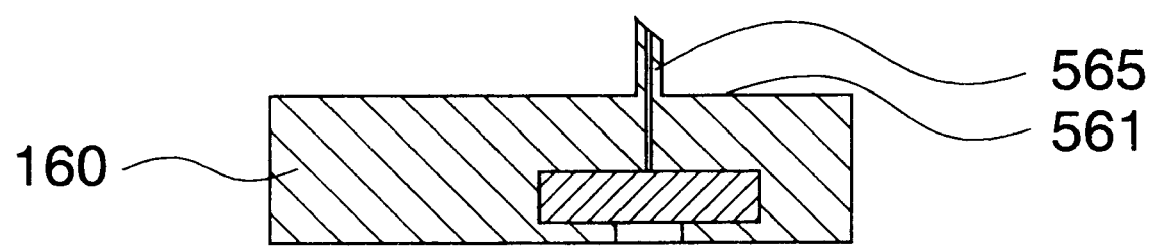

As shown in FIG. 12, the reagent container side connection part 151 of the reagent container 150, which is hole-like is incorporated with the seal member 555 while the pump unit side connection part 161 of the pump unit 160 is provided with the hollow needle-like protrusion 565, and accordingly, the structures of the reagent container 150 and the pump unit 160 can be simplified, thereby it is possible to reduce the manufacturing cost.

Explanation will be made of a seventh embodiment with reference to FIGS. 13a and 13b.

Figure 13:
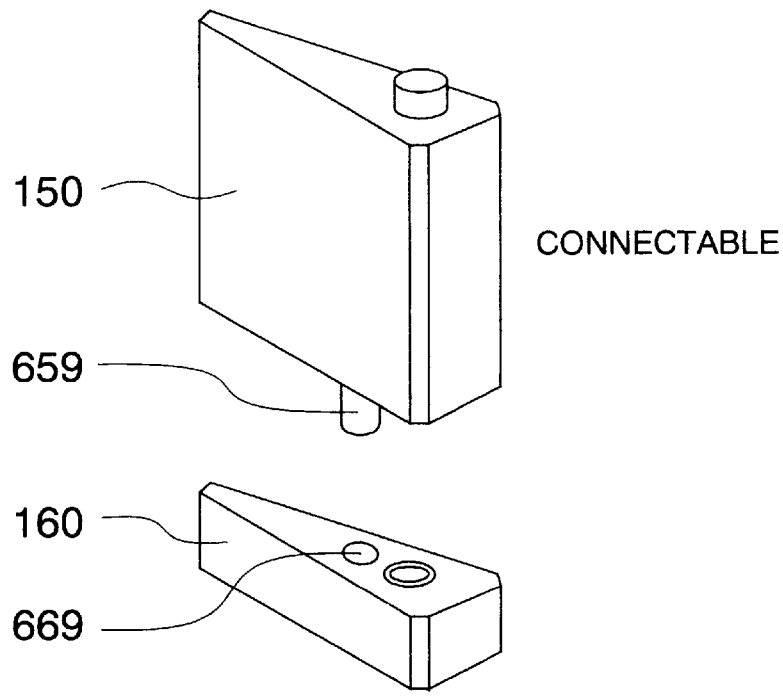
FIG. 13a is a perspective view illustrating a reagent container and a pump unit in a seventh embodiment of the present invention, which can be connected with each other.
FIG. 13b is a perspective view illustrating the reagent container and the pump unit shown in FIG. 13a, which cannot be connected with each other.
Figure 13:
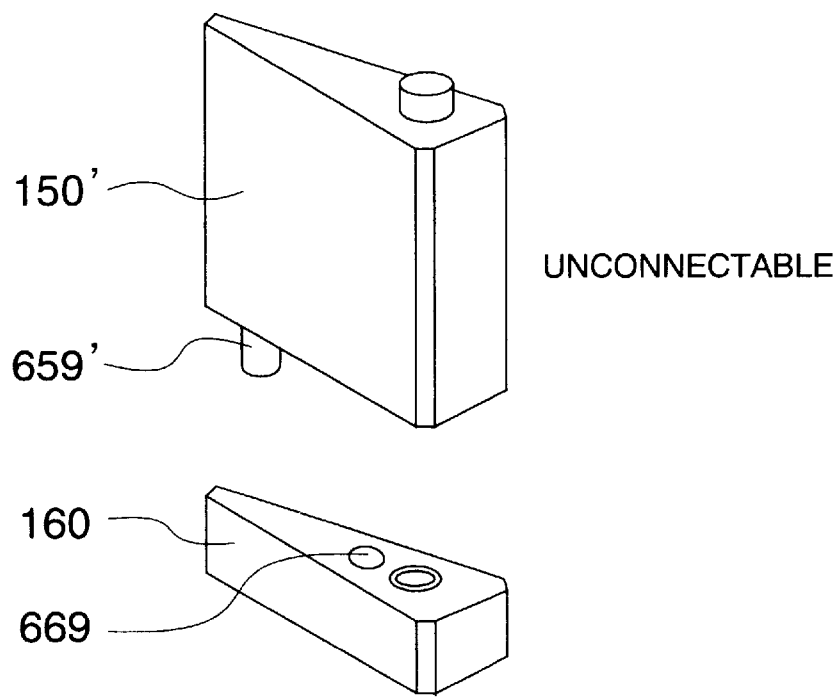

Referring to FIGS. 13a and 13b, the technique for preventing the pump unit 160 from being mounted to a reagent container 150 in which a reagent of a kind different from that of the reagent which has been used in this pump unit 160, is charged. It is noted that the arrangement of this embodiment is the same as that of the first embodiment, except that a protrusion is provided on the surface of the reagent container on the side opposed to the pump unit 160, and a hole adapted to be engaged in the protrusion when the pump unit 160 is mounted is formed.

As shown in FIGS. 13a and 13b, there are provided the pump unit 160 formed at its mounting surface with a recess 669, the reagent container 150 formed with a protrusion 659 at a position where it faces the recess 669 upon the mounting, and a reagent container 150' formed with a protrusion 659' at a position other than the position where it faces the recess upon the mounting. It is noted that the diameters and the lengths of the protrusions 659, 659' are smaller than the diameter and the depths of the recesses, respectively.

The reagent container 150 and the pump unit 160 can be connected with each other since the protrusion 659 is located at a position where it can be received in the recess 669. However, the reagent container 150' and the pump unit 160 cannot be connected since the protrusion 659' is not at a position where it cannot be received in the recess 669.

As mentioned above, the mounting surfaces of the reagent container 150 and the pump unit have different shapes, it is possible to prevent any of containers in which different kinds of reagents are charged, from being mounted to one and the same pump unit, thereby it is possible to prevent cross-contamination between the reagents.

It is noted that, in addition to this embodiment, connection parts having different shapes or different connections may be used in order to obtain effects similar to those obtained in this embodiment.

Explanation will be hereinbelow made of an eighth embodiment of the present invention with reference to FIGS. 14 and 15.

Figure 14:
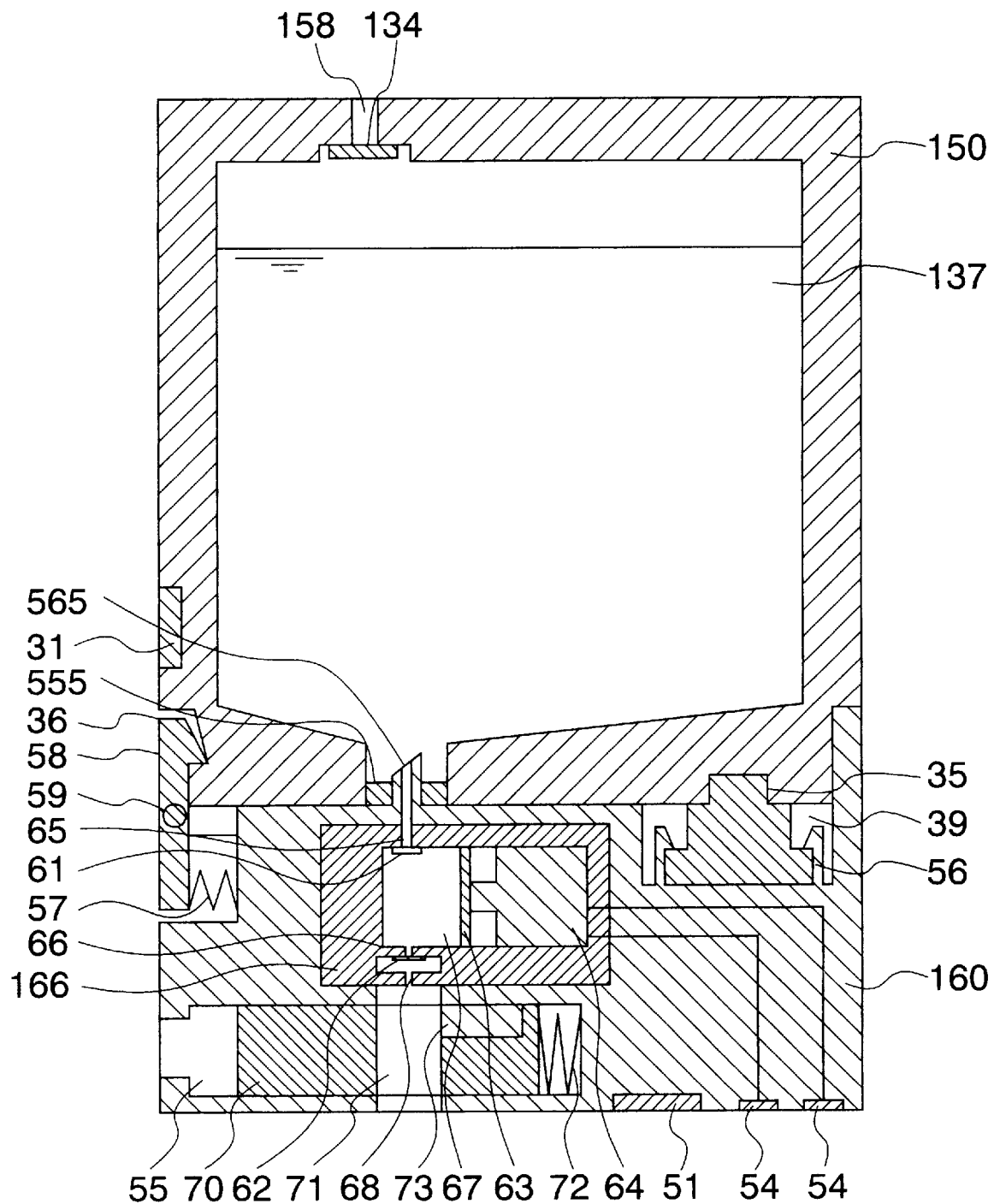
FIG. 14 is a sectional view illustrating a reagent container and a pump unit in an eighth embodiment of the present invention.
Figure 15:
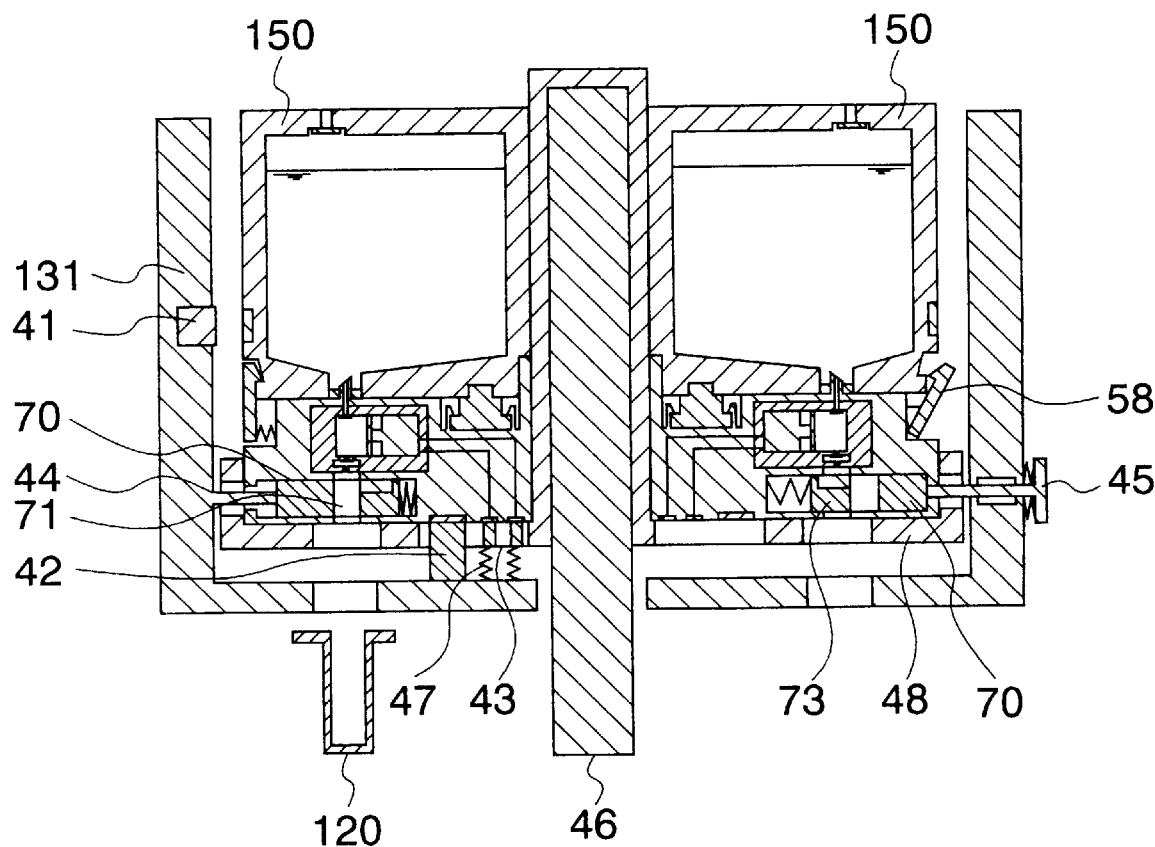
FIG. 15 is a detailed sectional view for explaining the reagent container and the pump unit shown in FIG. 14.

FIG. 14 is an enlarged view which shows the reagent container 150 and the pump unit 160, and the FIG. 15 is a sectional view illustrating the reagent container 150 and the pump unit 160 including a part of the reagent holder, at the reagent discharge position 190 and a reagent container position 191 in opposite to the former position.

Referring to FIG. 14, the reagent container 150 is formed in the upper part thereof with a suction port 158 for supplying a reagent 137, and a check valve 134 is provided in the suction port 158 so as to prevent the reagent 137 from leaking outside of the reagent container. Further, the reagent container 150 is provided in its lower part with a seal member 555 made of resilient material such as rubber and located in the reagent outlet port, for simplifying and ensuring the connection between the reagent container 150 and the pump unit 160, similar to that shown in FIG. 11. Further, in this embodiment, the reagent container 150 is formed at the outer periphery with a fixing part 36 which is adapted to be engaged with a fixing pawl 58 formed on the pump unit 160 so as to couple the reagent container 150 and the pump unit 160 with each other.

Further, in order to allow the reagent container 150 to be used and the pump unit 160 to fall in the same condition, an attaching part 35 adapted to be engaged with an attachment 39 is formed in the bottom part of the reagent container. Further, a recording medium 31 is provided in a part of the side surface of the reagent container 150, which will be detailed later.

Next, the pump unit 160 incorporates a positive displacement type reciprocating pump part 166 for sucking the reagent 137 from the reagent container 150 into a pump unit casing, and then for supplying the reagent 137 into the reaction container 120. Further, the casing is provided in its side part with a fixing pawl 58 adapted to be engaged with the reagent container 150. This fixing pawl 58 is supported at its one end by a resilient member 57 such as a spring or rubber so as to be swingable about the axis 59. Further, an attaching pawl 56 for fixing the attachment 39 which can distinguish a reagent container 150 to be used, is provided in the upper part of the casing. Moreover, a door 70 is a provided in the lower part of the reagent supply port 68 of the pump unit 160. Further, a recording medium 51 is provided in the lower part of the pump unit 160.

Explanation will be made of several parts in detail.

The pump part 166 is composed of a passage which is communicated with the pump unit casing and which is formed in the hollow needle-like protrusion 565, a suction port valve 61 provided in the passage on the side near to the reagent chamber 67, a discharge port 66 for discharging the reagent from the reagent chamber 67, a discharge port valve 62 provided in the distal end part of the discharge port 66, a partition wall 63 defining the reagent chamber 67, a drive source 64 for deforming the partition wall 63 so as to change the volume of the reagent chamber 67 for sucking and discharging the reagent into the reagent chamber 67, and a reagent supply port 68 provided in the distal end part of the discharge port valve 62.

The drive source 64 is connected to an electrode 54 provided to the pump unit casing through the intermediary of wiring, and accordingly, electric power is fed to the drive source 64 through the electrode 54.

In the operation of the pump unit 166, when the partition wall 63 is displaced or deformed by the drive source 64 in a direction in which the volume of the reagent chamber 67 is increased, the pressure of the reagent chamber 67 is lowered so as to open the suction port valve 61. When the suction port valve 61 is opened, the reagent 137 flows into the reagent chamber 67 through the reagent outlet port of the reagent container 150, a cylindrical reagent inlet port 565 of the pump unit 160 and the suction port 65 of the pump part 166. At this time, the discharge port valve 62 is still closed. When the partition wall 63 is displaced or deformed so that the volume of the reagent chamber 67 is decreased, the reagent 137 flows from the reagent chamber 67 and through the discharge port 66. The reagent 137 then flows out from the pump unit 160 through the reagent supply port 68 and an opening 71 in the door 70, and is supplied into the reaction container 120 located at the supply position. At this time, the suction port valve 61 is still closed.

Thus, the reagent 137 flows through the reagent outlet port of the reagent container 150, the suction port 65, the reagent chamber 67, the discharge port 66, the reagent supply port 68 and the opening 71 in the mentioned order, and is then supplied into the reaction container 120. Thus, without moving the pump unit 160 located at the supply position, the reagent 137 can be supplied into the reaction container located at a shortest position, through a shortest passage. Thereby it is possible to supply the reagent from the reagent container into the reaction container 150 in a short time.

It is noted that an axial flow type pump, a positive displacement type rotary gear pump or a variable vane pump may be used in the pump part 166 of the pump unit 160. In particular, the positive displacement type rotary gear pump and the variable vane pump can exhibit the similar effects even though the suction port valve and the discharge port valve are not used. Further, a diaphragm micro pump may also be used.

As shown in FIG. 15, the supply of power to the drive source 64 of the pump part 166 is made through the wiring electrically connected to an electrode 43 in the automatic analysis apparatus and passing through a terminal 54 of the pump unit 160. In this arrangement, the electrode 43 is urged toward the terminal 54 by a repulsive force of a spring 47, that is, it is electrically connected but is not mechanically connected, and accordingly, when the reagent container disc 48 is rotated, the power can be applied to the pump unit which has come to the supply position 190.

It is noted that if magnetic force is used as a power for the drive source 64, an electromagnetic coil is located in the apparatus, while optical power is used, a light source is provided in the apparatus. Further, if sound wave is used as power, a sound source is provided in the apparatus while if heat is used as the power, a heat source is provided in the apparatus.

Similar effects can be obtained even thought the drive source 64 is removably mounted on the pump unit 160.

In this embodiment, the reagent container and the pump unit are adapted to be attached to the reagent container disk 48 provided in the reagent holder 131 or 141. In this arrangement, the reagent container holder is secured to the body of the automatic analysis apparatus while the reagent container disc is rotated.

The reagent outlet port is formed so that it comes to a lowest position when the reagent container 150 is mounted to the reagent container disc 48, and the bottom surface of the reagent container in which the reagent outlet port is formed has a slope so that the it is lower at the reagent outlet port. With this arrangement, even through the remaining quantity of the reagent 137 becomes less, the reagent is collected in the pump unit 160 by its dead weight, thereby it is possible to completely use the reagent without being wasted.

The seal member 155 made of an elastic material is located in the reagent outlet port of the reagent container 150. Accordingly, effects similar to that obtained by the arrangement shown in FIG. 11 can also obtained.

A check valve 134 provided in the suction port 158 of the reagent container 150 is opened when the quantity of the reagent 137 is decreased being discharged by the pump unit 160, and accordingly, air flows into the reagent container through the suction port 158 so as to restrain the pressure in the reagent container 150 from being lowered, thereby it is possible to restrain the reagent from counter-flowing from the pump unit 160 or to prevent the supply volume of the reagent from varying.

It is noted that similar effects can be obtained even though fibers coated over their outer surfaces with fluororesin having a high degree of water repellency are arranged, instead of the check valve.

The reagent container 150 is provided with an attaching part 35 adapted to be connected with the attachment 39, and the pump unit is provided with an attaching pawl 56 for fixing the attachment 39. In this arrangement, shapes of connection parts of the attachment 39 and the attaching parts 35 which are made into contact with each other, are different in dependence upon kinds of reagents. Further, the attachment 39 attached to the pump unit 160 is fixed by the attaching pawl 56. Accordingly, the attaching part fixed to the pump unit 160 has a part adapted to make contact with the attaching part 39 and having a shape which is different in accordance with kinds of reagents, and only a reagent container containing the same kind of reagent can be used when the reagent container is replaced with another. Accordingly, it is possible to prevent the reagent container from being erroneously mounted, thereby it is possible to prevent contamination between different reagents.

It is noted that the similar effect can be obtained even though the parts of the reagent container 150 and the pump unit 160 which make contact with each other, are loosely fitted together, and parts of the erg a attachment 39 and the pump unit 160 which make contact with each other are interference-fitted together.

The pump unit 160 is provided with the stationary pawl 58 which can be rotated around the shaft 59 as a rotary shaft, and further, which has a wedge-like shape on one side of the shaft 59, where it makes contact with the reagent container 150, and a spring 57 is provided on a side of the shaft 59 where it does not make contact with the reagent container 150 while a fixing part 36 is formed in the reagent container 150. Upon connection between the reagent container 150 and the pump unit 160, the repulsive force of the spring 57 is effected so that a part of the fixing pawl 58 wedges into the fixing part 36 in order to fix the reagent container 150 to the pump unit 160.

It is noted the similar effects can be obtained even though the pawl 58 on one side of the shaft 59 where it make contact with the reagent container 150 has a convex shape. Further, the similar effect can be obtained even though the spring 57 may be provided on a side of the shaft 57 where it make contact with the reagent container 150 so that the tension force of the spring 57 is effected. Further, the similar effects can be obtained even though the fixing pawl 58 is formed of a leaf spring with no use of the shaft 59 and the spring 57.

When an emptied reagent container 150 is replaced with a filled reagent 150, a button 45 is depressed at the nondischarge position 191, and the fixing pawl 58 is turned so as to release the fixing pawl 58 from the fixing part 36 while fixing the pump unit 160, thereby it is possible to remove only the reagent container 150. Further, the reagent container 150 filled with the reagent is mounted to the pump unit 160 accommodated in the reagent container disc 150. Thus, the reagent container can be replaced with another one without removal of the pump unit 160 from the reagent container disc 48.

It is noted that the above-mentioned steps are carried out manually, but a series of steps can be automatically made with the similar effects being obtained.

Next, explanation will be made of a condition in which the reagent container holder 131 is mounted with the reagent container 150, with reference to FIG. 15.

The reagent container 150 is provided with a reagent data recording medium 31 which stores therein data of a reagent, magnetically, electrically or optically. Further, the pump unit is provided with a pump unit data recording medium 51 (refer to FIG. 14) which stores therein data of a pump unit, magnetically, electrically or optically. Data stored in the reagent data recording medium 31 and including a kind of reagent and a manufacturing date of reagent, are transmitted from a reagent data reader 41 to a main controller (which is not shown). Data stored in the pump unit data recording medium 51 and including a manufacturing date, a used condition and a performance of the pump unit are transmitted from a pump unit data reader/writer 42 to the main controller. Further, data of a reagent read by the reagent data reader 41, a used condition of the pump unit 160, a remaining quantity of the reagent and the like are written in the pump unit data recording medium 51 by the pump unit data reader/writer 51. Accordingly, the management of reagents and the pump unit can be facilitated.

It is noted that the reading and writing of the above-mentioned data are made at the supply position 190. Even if the reagent data reader 41 and the pump unit data reader/writer 51 are additionally provided positions other than the above-mentioned position, data can be read and written simultaneously among a plurality of reagent containers 150 and pump units 160. Further, during replacement of the reagent container, data of a kind of reagent written in the reagent data recording medium 31 and a kind of reagent written in the pump unit data recording medium are verified with each other so as to prevent erroneous mounting of a reagent container, thereby it is possible to completely eliminate contamination between different kinds of reagents. It is noted that although it has been explained that the data recording mediums are provided to both the reagent container and the pump unit, the technical effects of the present invention can be also obtained even if the recording medium is provided to only the reagent container.

The pump unit 160 is provided with the door 70 which is movable along the guide 55. At the nonsupply position 191, the door 70 is urged by a repulsive force of a spring 72, and accordingly, the opening 71 is separated from the reagent supply port 68. Further, a seal member 558 made of elastic material and formed in the door 70 blocks the reagent supply port 68, and accordingly, isolates from the ambient air. At the supply position 190, a switch 44 provided on the reagent container holder 131 presses and displaces the door 70 so that the opening 71 formed in the door 70 is communicated with the reagent supply port 68 which is therefore exposed to the ambient air. Thus, the reagent can be supplied into the reaction container 120. With this arrangement, it is possible to prevent sticking of dust, contamination or the like to the reagent supply port 68, deposition of solid components of the reagent due to drying of reagent or the like. Thus, clogging of the reagent supply port, and entry of foreign matter into the reagent can be prevented during the supply of the reagent.

It is noted that the similar effects can be obtained even if the door 70 is automatically displaced by an actuator provided in the pump unit 160. Further, in such a case that moisture may be fed into a space defined in the reagent supply port 68 by the seam member 555 which blocks the former, by means of a humidifying mechanism installed in the automatic analysis apparatus so as to control the humidity in the closed space, it is possible to prevent the reagent from being dried.

Explanation will be made of a ninth embodiment of the present invention with reference to FIG. 16.

This embodiment is the same as that shown in FIG. 15, except that a reagent bag 80 is provided in the reagent container 150, and a shut-off vale 81 is provided in the lower part of the reagent container 150, instead of the seal member 555 while an O-ring 38 is provided for sealing.

The reagent bag 80 is filled therein a reagent with no gas contained therein. Further, the internal volume of the reagent bag 80 changes in accordance with a quantity of reagent stored therein. With this arrangement, it is possible to prevent gas from entering the pump unit 160, thereby it is possible to maintain a supply volume of reagent with a high degree of accuracy during pipetting thereof.

Figure 16:
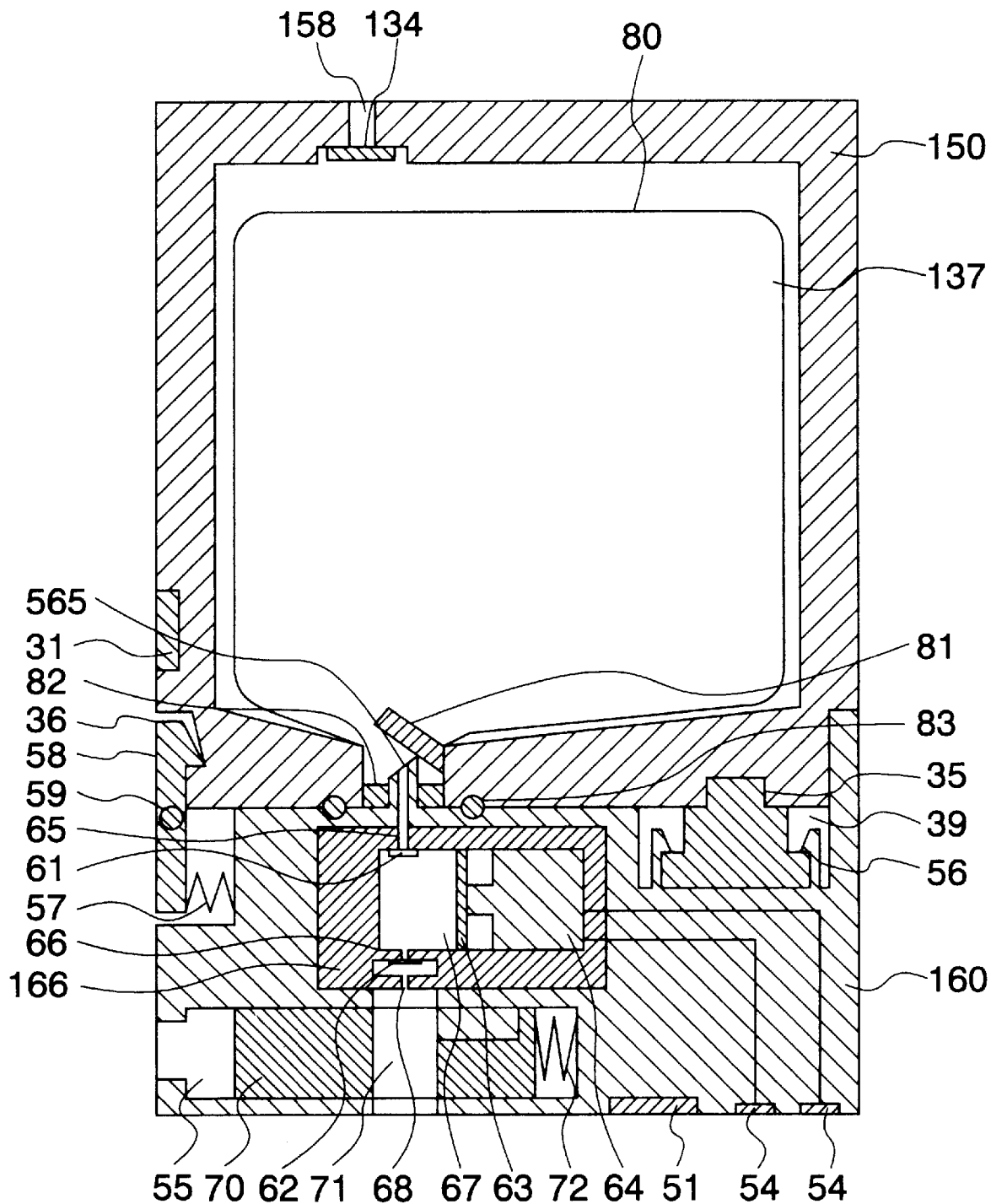
FIG. 16 is a sectional view for explaining a reagent container in a ninth embodiment of the present invention.

FIG. 16 shows a condition in which the reagent container 150 is mounted to the pump unit 160, the shut-off valve 81 is pressed by the reagent inlet port 52 so as to be separated from the bottom 82 of the reagent outlet port, and accordingly, the reagent container 150 is communicated with the pump unit 160. The O-ring 83 provided in the pump unit 160 seals between the reagent container and the pump unit 160. Before the reagent container 150 is mounted to the pump unit 160, the shut-off valve 81 is made into close contact with the bottom 82 of the reagent outlet by means its spring action for sealing. Thus, with the provision of the shut-off valve 81 in the reagent outlet port 32 in a simple structure, the reagent can be prevented from leaking through the reagent outlet port 32 before the reagent container 150 is mounted on the pump unit 160, and the reagent container 150 can be surely communicated with the pump unit after the reagent container 150 is mounted to the pump unit 160.

With the provision of such an arrangement that the reagent container and the pump unit is removably attached to each other, it is possible to prevent cross-contamination between different kinds of reagents. Further, if the reagent container is discarded after use, it is possible to reduce the cost of the reagent container, and it is possible to reduce the quantity of waste. Further, in the case of reuse of the reagent container and the pump unit, since the reagent container is alone washed, the consumption of washing liquid and detergent can be reduced, and further, the washing time can be shortened.

Further, according to the present invention, there is provided the positional device preventing mechanism (that is, the fixing plate is provided to the pump unit, and the connection part is formed with threads), for preventing positional deviation.

Further, the reagent container side connection part of the reagent container is hole-like, and is incorporated together with the seal member, and the pump unit side connection part of the pump unit is formed of a hollow needle, the structures of the reagent container and the pump unit can be simplified, thereby it is possible to reduce the manufacturing cost.

Further, the surface of the reagent container by which it is mounted to the pump unit has a shape which is different in dependence upon a kind of reagent to be used, it is possible to prevent reagent containers containing different reagents from being mounted to one and the same pump unit, and accordingly, it is possible to prevent cross-contamination among different reagents.

The supply of power to the drive part of the pump unit is made through the electrode which is pressed against the terminal by a repulsive force of the spring, and accordingly, the drive part is electrically connected to the power source but is not mechanically made connected thereto, thereby it is possible to supply power to arbitrary one of the reagent containers, having conveyed to the supply position through the rotation of the reagent container disc.

The reagent outlet port is located at a lowest position when the reagent container is mounted on the reagent container disc, and the bottom surface in which the reagent outlet port is formed, has a slope so that the outlet side becomes lower, and accordingly, the reagent is collected in the reagent supply device under gravitational force even though the quantity of the reagent becomes slight, thereby it is possible to completely use the reagent with no waste.

The check valve is provided in the suction port of the reagent container, and accordingly, the pressure in the reagent container can be restrained from being increased while the counter-flow of the reagent and variation in the quantity of the reagent can be prevented.

The data recording mediums are provided in the reagent container and the pump unit, respectively, and data concerning a kind of reagent, a used condition, a manufacturing date or the like are transmitted form the data reader to the main controller, thereby it is possible to facilitate handling of the read data such as a use condition of the reagent supply device, and it is possible to facilitate the management of thus read data as to the reagent, and a use condition of the reagent supply device, a remaining quantity of the reagent or the like.

What is claimed is:

1. An automatic analysis apparatus comprising a plurality of reaction containers, a sample supply a means for supplying a sample into each of said reaction containers through an opening formed in an upper part of said reaction container, reagent containers for exclusively holding plurality kinds of reagents therein, respectively, a reagent supply means for supplying a predetermined quantity of a reagent from each of said reagent containers into each of the reaction containers through the opening formed in the upper part of thereof, and a measuring means for measuring a physical property of said sample during reaction or after completion of reaction in said reaction container, characterized in that said reagent supply means is composed of a pump unit which is mounted to a lower part of each of said reagent containers in the automatic analysis apparatus so as to pipette said reagent;

wherein said reagent container and said pump unit are connected together through connection components thereof and having portions which contact one another, and wherein at least one of said portions of said pump unit and said reagent container has a shape which is different in accordance with a kind of a reagent reserved in said reagent container.

2. An automatic analysis apparatus as set forth in claim 1, wherein a fixing recess is formed in said reagent container, and a fixing panel for engagement is provided to said pump unit.

3. An automatic analysis apparatus as set forth in claim 1, wherein said connection parts of said pump unit and said reagent container are formed with thread components which are meshed with each other.

4. An automatic analysis apparatus as set forth in claim 1, wherein said reagent container is formed with an insertion guide corresponding to the shape of said pump unit.

5. An automatic analysis apparatus as set forth in claim 1, wherein a reagent supply port of said reagent container, for said pump unit, is provided with a seal member made of elastic materials, and a reagent supply port of the pump unit is in the form of a hollow needle.

6. A automatic analysis apparatus as set forth in claim 1, a data recording medium is provided to either said pump unit or said reagent container, and a data recorder/reproducer is provided at a position opposed to said data recording medium, said data recorder/reproducer at least one of reads and writes data from and to said data recording medium.

7. An automatic analysis apparatus as set forth in claim 1, wherein said connection components through which said reagent container and said pump unit are connected are provided with said portions including a protrusion and a recess, respectively, for distinguishing a kind of reagent.

8. An automatic analysis apparatus comprising a movable reaction container holder for accommodating a plurality of reaction containers, a sample supply means for supplying a sample into each of said reaction containers at a predetermined position, reagent containers reserving therein with plural kinds of reagents, respectively, a reagent holder for accommodating therein said reagent containers and for displacing said reagent containers; a reagent supply means for supplying a predetermined quantity of reagent from each of said reagent containers into each of said reaction containers, and a measuring means for measuring a physical property of said sample in said reaction container in which said reagent is added, characterized in that said reagent supply device is composed of a pump unit which is removably attached to a lower part of each of said reagent container which is then installed on said reagent holder with the pump unit being arranged underneath the reagent container, wherein the reagent is supplied into the reaction container at a predetermined position, wherein an operable door is provided in a reagent supply port of said pump unit, and said reagent supply port is closed by said door when no reagent is discharged, and said door is opened when the reagent is discharged.

9. An automatic analysis apparatus as set forth in claim 8, wherein data recording mediums are provided to said pump and the reagent containers, respectively, and data recorder/reproducers being provided at a position opposed to said recording mediums, said data recorder/reproducer at least one of reads and writes data from and to said recording mediums.

10. An automatic analysis apparatus as set forth in claim 8, wherein a reagent bag in which the reagent is filled is provided in said reagent container.

11. An automatic analysis apparatus as set forth in claim 8, wherein said reagent container and said pump unit are connected together through connection components thereof and having portions which contact one another, and wherein at least one of said portions of said pump unit and said reagent container has a shape which is different in accordance with a kind of a reagent reserved in said reagent container.

12. An automatic analysis apparatus as set forth in claim 8, wherein a reagent outlet port is formed in said reagent container at a lowest position of said reagent container when said reagent container is installed on said reagent holder, and said reagent container is formed with a slope so that a bottom surface of said reagent container in which said reagent outlet port is formed is lower on said reagent port side.

13. An automatic analysis apparatus as set forth in claim 8, wherein said reagent holder is formed therein with a rotatable reagent container disc, and said reagent container disc is rotated so as to change the position of said reagent container.

\* \* \* \* \*